United States Patent [19]

Brühne et al.

[11] 4,229,379

[45] Oct. 21, 1980

[54] PROCESS FOR THE PREPARATION OF BENZALDEHYDE

[75] Inventors: Friedrich Brühne; Karl-August Lipper, both of Krefeld, Fed. Rep. of Germany

[73] Assignee: Bayer Aktiengesellschaft, Leverkusen, Fed. Rep. of Germany

[21] Appl. No.: 958,240

[22] Filed: Nov. 6, 1978

[30] Foreign Application Priority Data

Nov. 25, 1977 [DE] Fed. Rep. of Germany ....... 2752612

[51] Int. Cl.³ .............................................. C07C 45/43
[52] U.S. Cl. .................................................... 568/437
[58] Field of Search ................................ 260/599, 600

[56] References Cited

U.S. PATENT DOCUMENTS

| | | | |
|---|---|---|---|
| 3,499,934 | 3/1970 | Pyne | 260/599 |
| 3,524,885 | 8/1970 | Deinet | 260/599 |
| 3,624,157 | 11/1971 | Ingwalson et al. | 260/599 |
| 3,700,736 | 10/1972 | Yamamoto et al. | 260/599 X |

*Primary Examiner*—Bernard Helfin
*Attorney, Agent, or Firm*—Sprung, Felfe, Horn, Lynch & Kramer

[57] ABSTRACT

An improved process for the preparation of benzaldehyde by hydrolysis of benzal chloride wherein hydrolysis is carried out at an elevated temperature in the presence of an excess of aqueous hydrochloric acid and in the absence of another catalyst.

3 Claims, No Drawings

PROCESS FOR THE PREPARATION OF BENZALDEHYDE

The present invention relates to an improved process for the preparation of benzaldehyde from benzal chloride.

The action of water on benzal chloride at 140° to 160° C. with the formation of benzaldehyde is already described in Liebigs Ann. Chem. 139, 319 (1866). However it is emphasised that the benzaldehyde is formed in varying amounts. The conversion into benzaldehyde is said to take place more readily when 1 mol of benzal chloride is warmed to 50° C. with 2 mols of concentrated sulphuric acid and, after the evolution of HCl has ended, the mixture is diluted with water (Beilstein, volume 5, page 298, 1st paragraph (1922)). This process has the disadvantage, however, that large amounts of dilute sulphuric acid are formed as a waste product. There is also the danger of the formation of sulphonated and oxidized by-products.

The known industrial processes for the preparation of benzaldehyde by the saponification of benzal chloride with water make use of the catalytic activity of Friedel-Crafts catalysts and specific amines. Thus, for example, it is recommended to saponify benzal chloride at elevated temperature in the presence of catalytic amounts of zinc chloride (German Auslegeschrift No. 1,153,009), zinc phosphate (U.S. Pat. No. 3,524,885), ferric chloride (German Auslegeschrift No. 2,044,832) or specific organic amines (Japanese Laid-Open Specification No. 12,132/69). The saponification times can indeed be considerably shortened by using the catalysts, but in return there is the disadvantage of expensive working up of the mother liquors in order to remove the metal compounds or amine hydrochlorides from the effluent. Furthermore, the catalysts lead to the formation of varying amounts of polymeric by-products, by which means the yield is decreased.

In another process (German Auslegeschrift No. 2,261,616), dichloromethyl compounds are hydrolysed in the presence of relatively large amounts of phosphoric acids or sulphonic acids as catalysts. With these catalysts also, the formation of polymers during the saponification cannot be completely suppressed. This process permits recycle and re-use of the catalyst solution several times. The amount of effluent obtained is indeed thereby decreased, but since the aldehyde phase is washed only with a small amount of water (18 g of water for about 106 g of benzaldehyde), it is unavoidable that catalyst amounts of up to 0.5% remain in the crude benzaldehyde and these lead to further formation of polymers and residues during the required purification by distillation.

A process has been found for the preparation of benzaldehyde by the hydrolysis of benzal chloride, which is characterised in that the hydrolysis is carried out at elevated temperature with an excess of aqueous hydrochloric acid in the absence of other catalysts.

After the saponification process, the benzaldehyde prepared according to the invention is obtained in high purity, since it contains neither catalyst residues nor significant amounts of polymer which cannot be distilled, so that for many fields of use purification by distillation can be dispensed with. The present process furthermore is not harmful to the environment and is economical, since no effluents polluted with organic amines, heavy metals or phosphorus-containing compounds and sulphur-containing compounds are formed which, for reasons of maintaining the purity of water, must be subjected to expensive purification.

It is to be described as decidedly surprising that it is possible to prepare benzaldehyde in relatively short reaction times with high yields and in high purity under the conditions of the reaction according to the invention, which are not harmful to the environment. This was not to be expected with regard to the state of the art. It is known to prepare phthalaldehydic acid by hydrolysing $\alpha, \alpha, \alpha, \alpha', \alpha'$-pentachloro-o-xylene with a stoichiometric excess of water, which optionally contains HCl, in the absence of catalytically active salts at temperatures between 120° and 200° C. under the autogenous pressure of the reaction (German Offenlegungsschrift No. 2,529,038). Apart from the fact that the phthalaldehydic acid is obtained in a yield of only about 80% of theory, the saponification of the dichloromethyl group of $\alpha,\alpha,\alpha,\alpha',\alpha'$-pentachloro-o-xylene takes place in the presence of the carboxyl group intermediately formed, in the ortho-position, which, as is known from the literature (J. Org. Chem. 38, page 179-180 [1973]), acts an internal saponification catalyst. In other words, in contrast to the saponification, according to the invention, of benzal chloride, the saponification of the dichloromethyl group of $\alpha,\alpha,\alpha,\alpha',\alpha'$-pentachloro-o-xylene takes place in the presence of an internal catalyst.

The amount of hydrochloric acid in the process according to the invention should be chosen so that the amount of water present in the hydrochloric acid is 6 to 40 times, preferably 10 to 25 times, the stoichiometric amount required for the saponification of benzal chloride. If the excess of water is less than 6 times the stoichiometrically required amount of water, the saponification times are uneconomically long, whilst if the excess of water exceeds 40 times the amount of water required, the saponification times are short but the yields of benzaldehyde per reaction volume are low and thus uneconomic.

The HCl concentration of the aqueous hydrochloric acid used can vary within wide limits. In general, the HCl concentration is 2 to 39% by weight, preferably 10 to 33% by weight. In the particularly preferred embodiment of the process, the aqueous hydrochloric acid obtained during the hydrolysis is recycled again into the process, the water consumed during the saponification being replaced at the rate at which it is consumed. In this case, when the reactor is operated continuously, an HCl concentration which depends on the reaction temperature and the reaction pressure is established in the reactor.

The hydrolysis is carried out by heating the mixture of benzal chloride and the aqueous hydrochloric acid to temperatures in the range from about 90° to about 240° C., preferably at 100° to 200° C., under normal pressure, and in some cases under increased pressure. Intensive mixing of the two phases has a favourable influence on the rate of reaction. After the reaction has ended, the two phases of the reaction products are separated in the customary manner. After replacing the amount of water consumed during the reaction, the aqueous hydrochloric acid can be recycled again into the process. The aldehyde is obtained in the pure form in this process. It can be employed for many fields of use without further purification, if appropriate after washing with dilute alkali solution. Subsequent purification by distillation can, of course, also be carried out.

The process can be advantageously carried out in a manner such that pure hydrogen chloride is formed as a by-product, which can be condensed to give 30% strength hydrochloric acid, for example by adiabatic absorption.

The hydrolysis of benzal chloride can be carried out in the presence of inert gases, such as, for example, nitrogen or carbon dioxide, in order to exclude oxygen, which can lead to oxidation of the benzaldehyde formed.

A particularly preferred embodiment of the process is characterised in that the reaction is carried out continuously in a reactor or in a cascade-like arrangement of several reactors connected to one another, preferably 2 to 6 reactors. Carrying out the process continuously offers advantages with regard to the expenditure on operation and the consumption of energy.

The benzaldehyde prepared by the process according to the invention is a valuable intermediate product for the preparation of, for example, dyestuffs, aroma substances, pharmaceuticals and plant protection agents (compare Ullmanns Encyklopädie der technischen Chemie, 4th edition, volume 8, page 347–348, Verlag Chemie, Weinheim 1974; and Kirk-Othmer, Encyclopaedia of Chemical Technology, 2nd edition, volume 3, page 363–364, Interscience Publishers, New York, London, Sydney 1964).

EXAMPLE 1

322 g (2 mols) of benzal chloride and 750 g of 25 percent strength hydrochloric acid are heated to the reflux temperature in a 1 liter three-necked flask with a stirrer, reflux condenser, gas inlet tube and thermometer, whilst stirring vigorously, and the mixture is kept under light reflux for 2 hours. A sump temperature of 106° C. is established. A weak stream of nitrogen is passed through the flask during the reaction. The off-gas escaping from the reflux condenser is absorbed in a washing tower, packed with Raschig rings, with 600 g of water, which are circulated by means of a pump. After cooling the mixture, 204.0 g of a light yellow coloured oil which, according to the titrimetric determination, contains 98.1% of benzaldehyde (=200.1 g of pure benzaldehyde) are obtained as the organic phase. This corresponds to a yield of 94.3% of theory. The benzaldehyde contains 0.06% of residue which cannot be distilled. Analysis of the benzaldehyde phase by gas chromatography gives a benzal chloride content of 0.1%. 680 g of 21.9 percent strength hydrochloric acid containing benzaldehyde as an impurity are obtained as the aqueous phase. The amount of hydrogen chloride obtained by saponifying the benzal chloride is 99.5% of theory.

In the next batch, the yield of benzaldehyde is increased to 97.6% of theory if the aqueous phase of the last batch is re-used, after filling up to 750 g with hydrochloric acid.

EXAMPLE 2

1,610 g (10.0 mols) of benzal chloride and 2,100 g of 30.2 percent strength hydrochloric acid are heated to 125° C. in an enamelled stirred autoclave in the course of 35 minutes and the mixture is kept at this temperature for 45 minutes, whilst stirring vigorously, during which a pressure of 30 atmospheres gauge is established. After cooling, the autoclave is let down and the two phases are separated. After washing twice with a total of 188 g of water, the organic phase gives 912 g of pure benzaldehyde (85.8% of theory) with a benzal chloride content of 0.1% and a content of residue which cannot be distilled of 0.06%. The aqueous phase and the wash water are combined and give 2,365 g of a 32.5 percent strength hydrochloric acid, containing benzaldehyde as an impurity, which is employed for the next batch (Example 3).

EXAMPLE 3

The experiment in Example 2 is repeated, but instead of the 30.2 percent strength hydrochloric acid, the aqueous phase from Example 2, combined with the wash water (a total of 2,360 g with a HCl content of 32.5%), is used. After washing the organic phase twice with a total of 188 g of water, 1,025 g of pure benzaldehyde (96.4% of theory) are obtained with a benzal chloride content of 0.1%, and a content of residue which cannot be distilled of 0.08%. After combining with the wash water, the aqueous phase gives 2,352 g of a 32.3 percent strength hydrochloric acid, which can be re-used for the next batch.

EXAMPLE 4

150 ml/hour (189.0 g/hour) of benzal chloride and 300 ml/hour (338 g/hour) of 25 percent strength hydrochloride acid are introduced, by means of a metering pump, into the first vessel of a cascade consisting of three reaction vessels with stirrers and reflux condensers, each vessel of which has a useful volume of 1.1. l. The reaction product from the first vessel flows freely, via an outlet in the side, into the second vessel, and from there into the third vessel. The contents of the three reaction vessels are stirred and kept simmering, a sump temperature of 105°–107° C. being established. The HCl off-gas escaping from the reflux condensers is combined and washed in a washing tower, packed with Raschig rings, used in countercurrent with the benzal chloride, which is circulated by means of a further pump. The product flowing out of the third vessel passes, via a condenser, into a separating vessel in which it is continuously separated into the two phases. As soon as the separating vessel is operating, the hydrochloric acid phase is recycled continuously into the first vessel, after replacing the water consumed during the reaction, instead of the 25 percent strength hydrochloric acid. 124.0 g/hour of a yellowish-coloured oil which, according to the titrimetric determination, contains 97.9% of benzaldehyde (=121.4 g/hour of pure benzaldehyde) are obtained as the organic phase. This corresponds to a yield of 97.5% of theory. The benzaldehyde contains 0.08% of residue which cannot be distilled, and the benzal chloride content is at most 0.2%.

What is claimed is:

1. In a process for the preparation of benzaldehyde by the hydrolysis of benzal chloride, the improvement which comprises carrying out the hydrolysis at a temperature of 100° to 200° C. under normal pressure or under increased pressure in the presence of aqueous hydrochloric acid such that the amount of water in the hydrochloric acid is 10 to 25 times the stoichiometric amount required for the saponification of benzal chloride, the hydrochloric acid having a concentration of 10 to 35 percent by weight, the process being carried out in the absence of another catalyst.

2. A process according to claim 1 wherein the hydrolysis is carried out continuously in a reactor or in a cascade-like arrangement of several reactors connected to one another.

3. A process according to claim 1 wherein the aqueous hydrochloric acid obtained after the hydrolysis is recycled again into the saponification process.

UNITED STATES PATENT AND TRADEMARK OFFICE
CERTIFICATE OF CORRECTION

PATENT NO. : 4,229,379
DATED : October 21, 1980
INVENTOR(S) : Friedrich Brühne, Karl-August Lipper It is certified that error appears in the above—identified patent and that said Letters Patent is hereby corrected as shown below:

Column 4, line 24, "chloride" should read --chloric--

Signed and Sealed this

Tenth Day of March 1981

[SEAL]

Attest:

RENE D. TEGTMEYER

*Attesting Officer*   *Acting Commissioner of Patents and Trademarks*